US008003768B1

(12) United States Patent
Gordon

(10) Patent No.: US 8,003,768 B1
(45) Date of Patent: Aug. 23, 2011

(54) SYSTEM FOR PROVIDING 20% ETHANOL SOLUTIONS THAT MEET BIOBURDEN AND ENDOTOXIN REQUIREMENTS

(75) Inventor: Tim Gordon, Bryn Mawr, PA (US)

(73) Assignee: Decon Labs, Inc., King of Prussia, PA (US)

( * ) Notice: Subject to any disclaimer, the term of this patent is extended or adjusted under 35 U.S.C. 154(b) by 523 days.

(21) Appl. No.: 11/482,177

(22) Filed: Jul. 5, 2006

(51) Int. Cl.
*A61L 2/18* (2006.01)
*C07K 1/22* (2006.01)
*C12M 1/00* (2006.01)
*C12Q 1/22* (2006.01)

(52) U.S. Cl. ............ 530/413; 141/5; 141/237; 210/670; 222/1; 222/189.06; 222/251; 422/28; 422/40; 435/31; 435/283.1; 435/287.3; 435/288.1; 436/18

(58) Field of Classification Search .................. None
See application file for complete search history.

(56) References Cited

U.S. PATENT DOCUMENTS

| 4,937,194 | A | * | 6/1990 | Pattillo et al. ............... 141/10 |
| 6,450,215 | B1 | * | 9/2002 | Willemstyn et al. ............ 141/10 |
| 6,913,695 | B2 | * | 7/2005 | Jones et al. .................... 210/635 |
| 2003/0080140 | A1 | * | 5/2003 | Neas et al. ..................... 222/1 |
| 2010/0056645 | A1 | * | 3/2010 | Deorkar et al. ................ 514/730 |

* cited by examiner

*Primary Examiner* — David A Saunders
(74) *Attorney, Agent, or Firm* — John F. A. Earley, III; Frank J. Bonini, Jr.; Harding, Earley, Follmer & Frailey, P.C.

(57) ABSTRACT

A system and method for providing 20% ethanol solutions meeting bioburden and endotoxin specifications, which provides the 20% ethanol solution in a ready-to-use form which may be dispensed directly from the container in which the solution is shipped, and which may be used in connection with storage, reuse and/or rejuvination of Protein A.

18 Claims, 2 Drawing Sheets

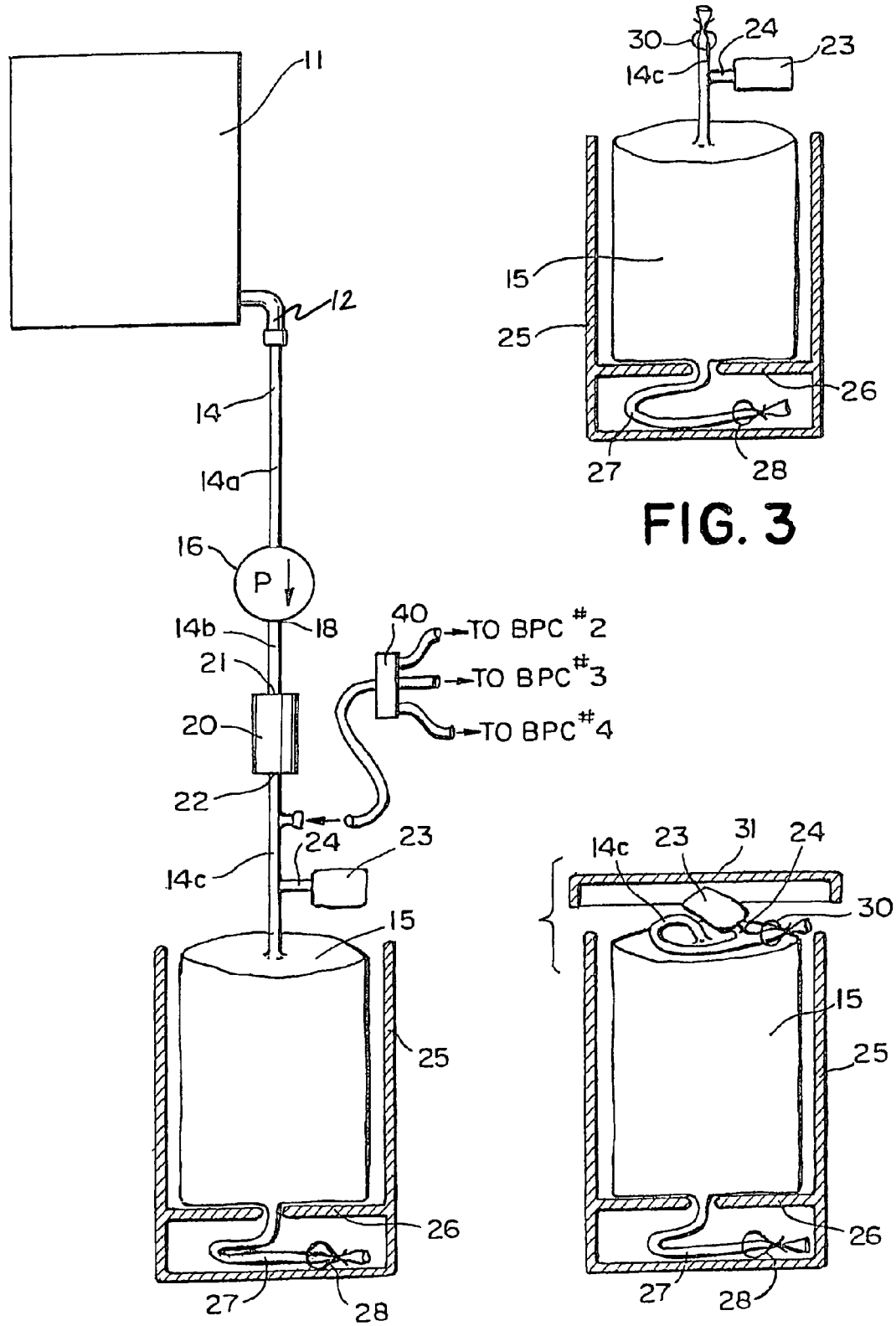

SYSTEM FOR PROVIDING 20% ETHANOL SOLUTIONS THAT MEET BIOBURDEN AND ENDOTOXIN REQUIREMENTS

BACKGROUND OF THE INVENTION

1. Field of the Invention

This invention relates to an improved system and method for providing 20% ethanol solutions meeting bioburden and endotoxin specifications useful for storing, reusing, and/or rejuvenating Protein A used in monoclonal antibody production.

2. Brief Description of the Related Art

Pharmaceutical and biotechnology companies produce monoclonal antibodies to manufacture cancer-specific drug products. The antibody products are purified by filtering them through substrate/media which is coated with Protein A, a product which is a cell wall constituent having binding affinity to the Fc portion of certain immunoglobulins. Protein A is instrumental in protecting against certain tumors, carcinogens, toxins, as well as certain fugal matter and parasites. Protein A is both important and expensive. However, through "cleaning", it can be reused and/or rejuvinated by cleaning and storing it in a 20% ethanol solution. Protein A therefore may remain stored between manufacturing runs where it may be needed. The 20% ethanol solution must meet certain requirements for satisfying bioburden and endotoxin levels. Bioburden is generally considered to be the population of viable microorganisms on a product or package. Endotoxin is sometimes also referred to as lipopolysaccharides which are present in cell membranes of Gram-negative bacteria (e.g., *E. coli*). Many DNA applications are endotoxin sensitive, and as a result endotoxins may reduce the transfection efficiency of endotoxin-sensitive cell lines.

The 20% ethanol solution required for use in connection with Protein A storage/rejuvination is prepared by using high quality water to dilute pure ethanol to a 20% solution, and then filtering the solution through a filter, such as a 0.22 micron filter, into a clean or sterile container. Using a 0.22 micron filter is a common practice to sterilize liquid solutions. Bioprocess containers, such as, for example, flexible plastic bags, are also utilized, such as for example, with intravenous solutions, which may also utilize tubing and an in-line filter.

There are drawbacks with the current ways in which 20% ethanol is obtained and utilized for the demands of those requiring a sterile solution meeting the specification for bioburden and endotoxin. Because of the specifications which may relate to sterility, ethanol is used, and regulations require 20% ethanol, and filtration requirements as well, such as, for example filtering though a 22 micron filter. In addition, testing for endotoxin is frequently done to ensure sterility, or that a product conforms to a particular sterility standard. Ethanol solutions may be used, and generally, they must conform to sterility requirements. Generally, ethanol is sold as pure ethanol. Companies who have a requirement for 20% ethanol, therefore, must purchase pure ethanol, and then from that make a 20% ethanol solution. When the 20% ethanol solution is used for a process which must meet bioburden and endotoxin specifications, the companies in addition to mixing pure ethanol with purified water to achieve the 20% solution, must then filter the solution, such as through a 0.22 um filter into a clean or sterile container. Storing the 100% ethanol on site and preparing the 20% ethanol solutions from the stored 100% ethanol when they are needed waste time, money and manufacturing resources of companies requiring 20% ethanol solution, since special equipment is required to store pure ethanol which is not needed to store 20% ethanol solutions, since manufacturing resources must be allocated to handling the pure ethanol and the production of 20% ethanol solutions which might otherwise be allocated to maximize finished drug production, for example, and since production might be slowed down awaiting production of the 20% ethanol solution. Further, a mistake made during the on site production of 20% ethanol solution may result in the solution not being usable, therefore wasting resources and shutting down production of a finished drug product whose production is dependant upon the 20% ethanol solution while a new batch of 20% ethanol solution is prepared to replace the unusable batch to which the mistake was made. Further, an unusable batch of ethanol solution, if mistakenly used in the production of a finished drug product, for example, may adversely affect bioburden and endotoxin levels, resulting non-conformity of materials used in the production of the finished drug product and/or the finished drug product itself. Also, steps must be taken to safely ship and store pure (100%) ethanol, since pure ethanol is considered flammable and must be handled and stored in a manner that meets federal, state and local guidelines for hazardous, flammable material.

A need exists for a system for providing a 20% ethanol solution which may be provided in a form which is directly usable and which still meets requirements for bioburden and endotoxin specifications. A system which is able to provide an end user with a 20% ethanol solution which meets the bioburden and endotoxin specifications, and can therefore be directly used by the end user without requiring the end user to dilute pure ethanol to a 20% ethanol solution, saves time and resources for the end user, and is safer to transport to the end user than pure ethanol.

SUMMARY OF THE INVENTION

It is an object of the invention to provide a method and system for storing, transporting, and delivering a 20% ethanol solution which may be used directly from the container in which the solution is shipped.

It is another object of the invention to provide a system for storing, transporting, and delivering a 20% ethanol solution which may be used directly from the container in which it is shipped, and which is suitable for use in applications which call for the solution to meet bioburden and endotoxin specifications and/or requirements.

Further, it is an object of the present invention to provide a safe and efficient system and method for storing, transporting, and delivering a 20% ethanol solution meeting the high standards for sterility for bioburden and endotoxin specifications, which may be used directly from the container in which it is transported for storage, reuse and/or rejuvination of Protein A.

These and other objects are accomplished by providing, in accordance with the invention, a system and method for providing 20% ethanol solutions meeting bioburden and endotoxin specifications which are in a form which may be readily used by an end user. The system includes a bioprocess container (BPC) which is generally provided in the form of a flexible plastic bag. The bag preferably has an opening for dispensing the 20% ethanol solution, and receives a length of tubing having an in-line filter through which contents may be dispensed into the bag. The 20% ethanol solution may be introduced into the bag through the tubing, and may also be dispensed from the bag through tubing.

The system enables a user to purchase, receive, store and use directly from the bag, the 20% ethanol solution which meets the specification requirements for bioburden and endotoxin. The system preferably includes a drum to protect the plastic bag, and the drum may have an opening for the outlet tubing to be accessed for dispensing the ethanol solution.

Ethanol is characterized as being highly flammable, and therefore must be stored, handled and disposed of in accordance with certain federal, state, and/or local regulations. An object of the present invention is to provide a safe and efficient system and method for delivering a 20% ethanol solution to an end user in a form which may be directly used by the end user, and which meets the high standards for sterility for bioburden and endotoxin specification.

BRIEF DESCRIPTION OF THE DRAWING FIGURES

FIG. 2 shows an apparatus, constructed in accordance with a preferred embodiment of the invention, which may be used in accordance with the system and method of the present invention.

FIG. 3 is a view of a container shown in cross-section, and bioprocess bag removed from the tubing and positioned in the container.

FIG. 4 is a view in cross-section of the container of FIG. 3, shown with a bioprocess bag secured therein and a lid being secured on the container.

DETAILED DESCRIPTION OF THE PREFERRED EMBODIMENTS

Figure 1:
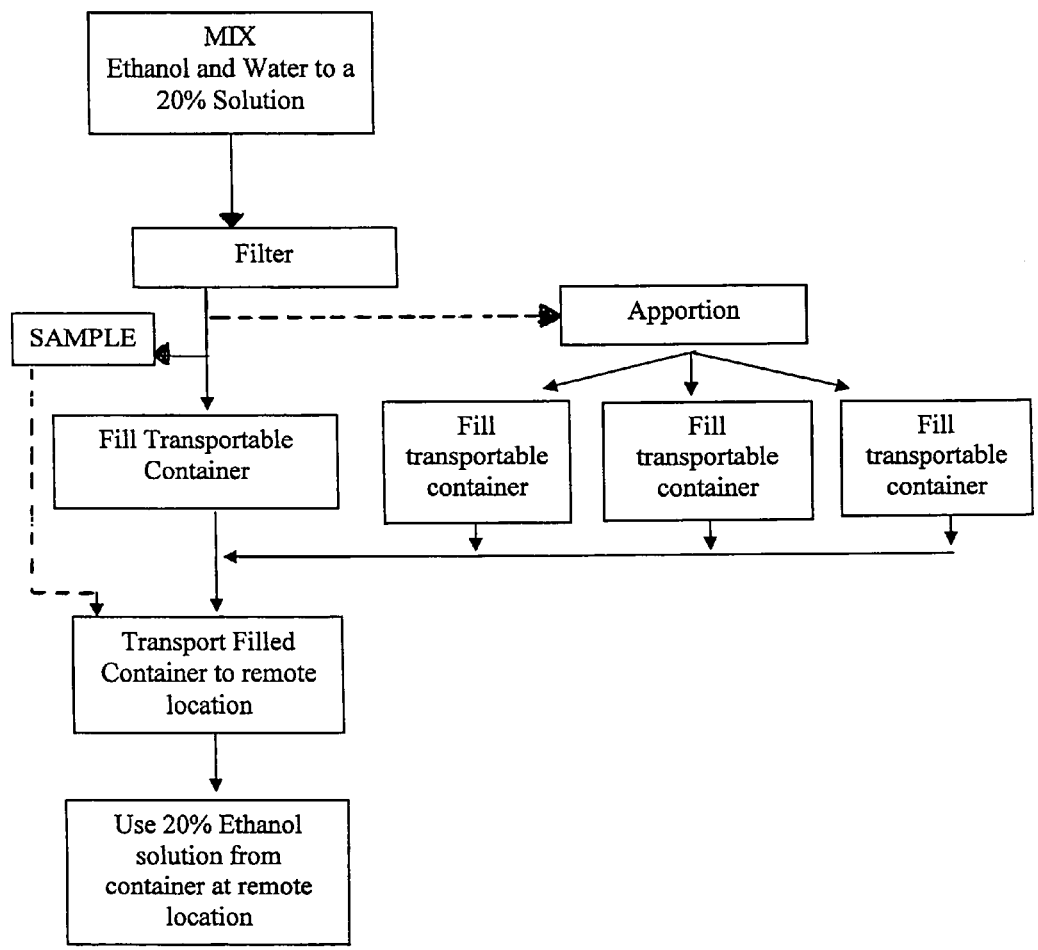
FIG. 1 is a flow diagram illustrating the system and method of the present invention.

The invention comprises a method and system for providing 20% ethanol solutions meeting bioburden and endotoxin specifications, which provides the 20% ethanol solution in a form which may be used directly from a container by an end user. The system has particular utility for providing a 20% ethanol solution which may be shipped, stored and dispensed from the same container by the end user, where the 20% ethanol solution is suitable for direct use by the end user in connection with the storage, reuse and/or rejuvination of Protein A. Protein A is a cell wall protein which exhibits unique binding properties to mammalian IgGs. Protein A increases the specificity for the molecule for IgG. Since Protein A is very expensive, it is generally reused or rejuvinated by placing it in a 20% ethanol solution. The system and method of the invention provide 20% ethanol solution which may be directly used with Protein A.

Referring to FIG. 1, a schematic diagram of the method and system according to an embodiment of the invention is illustrated. In accordance with the method and system, water is added with ethanol to make up a 20% ethanol solution. The 20% ethanol solution is filtered to remove impurities, including microbes. The 20% ethanol solution, once filtered, is dispensed into one or more transportable containers. Associated with each container preferably is a sample bag which is provided to represent the contents of the transportable container. The sample bag contents may be transported with the container containing the dispensed 20% ethanol solution, so that it may be tested prior to use, or may be retained at the filling location. Once transported to the remote location, the solution may be dispensed directly from the transportable container for use with Protein A.

Referring to FIG. 2, the system and method are illustrated with apparatus which may be used in accordance with the invention. A tank or vessel 11 for containing liquids is provided. A known amount of pure ethanol is placed into the vessel 11, and an amount of pure water, preferably USP purified water, is added to dilute the ethanol to a 20% ethanol solution. After mixing the ethanol and water together to form the ethanol solution, the ethanol solution is tested/assayed to verify that it meets the predetermined chemical specifications for a 20% ethanol solution. The vessel 11 preferably has an outlet port 12 which is connected to flow delivery means for delivering the 20% ethanol solution from the vessel 11 to a transportable storage means.

The flow delivery means is illustrated as tubing 14, which preferably may be flexible silicone tubing. The tubing 14 preferably may be provided as part of the transportable storage means. The transportable storage means receives the sterile 20% ethanol solution, and holds the solution therein, until the end user is ready to dispense it. As illustrated in FIG. 2, the transportable storage means comprises a bioprocess container (BPC) in the form of a flexible bag 15. In a preferred embodiment of the invention, the flexible bag 15 is sized to hold 55 liters of the 20% ethanol solution.

Pump means for pumping the 20% ethanol solution from the vessel 11 into the transportable storage means or bag 15 is provided along the flow delivery means. The pump means may comprise a peristaltic pump 16 which is connected to a first portion 14a of the tubing 14. The flow delivery means may include a second portion 14b of tubing 14. Filter means is also provided to filter harmful material from the 20% ethanol solution before the solution is dispensed into the bag 15. The filter 20 is preferably a 0.22 micron filter, such as, for example, a cartridge filter, which filters microbes from the solution. The second portion 14b of tubing 14 is connected to the pump outlet port 18 and the filter inlet port 21. The flow delivery means preferably includes a third portion 14c of tubing 14 which connects the filter outlet port 22 to the sample bag 15. Preferably, the third length 14c of tubing 14 may be integrally provided with the bag 15.

Preferably, sampling means is provided for receiving a sample of the 20% ethanol solution which is being dispensed into the bag 15. The sampling means is illustrated comprising a sampling bag 23, also a bioprocess container (BPC) but preferably smaller in volume than the transportable container means or bag 15. In a preferred embodiment of the invention, the sampling bag 23 is sized to hold 1 liter of the 20% ethanol solution. The sampling bag 23 preferably has integral sampling tubing 24 which connects with the third portion 14c of tubing 14, and may be integral therewith. The sample bag 23 may be detached from the flow delivery means, so it may be stored at the filling location, or stored and transported with the bag 15, or transported separately from the bag 15, as desired. Alternately, the sampling bag 23 may remain connected, and can be transported with the bag 15. Typically, the sampling bag 23 containing the 20% ethanol solution is sent to a testing lab for testing of the solution contained in the sampling bag 23 prior to the solution contained in the bag 15 being used.

The pump 16 pushes the 20% ethanol solution through the filter 20 and into the bag 15. When the bag 15 is filled, the bag 15, if not already in one, is placed into a protective storage container, such as a rigid drum 25. The drum 25 has a shelf 26 for holding the bag 15. Dispensing means, such as, for example, the dispensing tube 27 is provided, and as illustrated may be integral with the bag 15. The dispensing tube 27 may have a valve 28 or other suitable closure mechanism for permitting and closing off the flow of the solution from the bag 15.

Once the bag 15 is filled with the 20% ethanol solution, the third portion 14c of tubing 14 preferably is closed, by a suitable closure means, such as a clamp 30 or the like, as illustrated in FIG. 3. The third portion 14c of tubing 14 may then be cut above the clamp 30 or detached from the outlet port 22 of the filter 20, to transform the bag 15 into a closed system to ensure that the solution contained within the bag 15 remains within specifications for bioburden and endotoxin levels, and to free the bag 15 for transport. The portion 14c of the tubing 14 may be stored on the bag 15, as shown in FIG. 4, and a lid 31 placed on the drum 25 to secure the bag 15 within the drum 25. The drum 25 and bag 15 containing the 20% ethanol solution which meets the specifications for bioburden and endotoxin may be transported from the filling location (e.g., a distilled spirits plant) to a remote location (e.g., a pharma/biotech company). Preferably, the remote location is the location where the end user uses the 20% ethanol solution. The system and method provide the end user with access to the 20% ethanol solution for dispensing from the bag 15 as needed by the end user. The end user may dispense the 20% ethanol solution from the bag for reuse or rejuvination of Protein A. The invention provides for the safe transportation and storage of ethanol for use in connection with Protein A, and improves the efficiently of the reuse/rejuvenating and storage processes for Protein A by eliminating the step of requiring onsite production of a 20% ethanol solution.

The system and method preferably may be employed to provide multiple bags 15 which are filled from the vessel 11. Optionally, as illustrated in FIG. 2, manifold means such as the manifold 40 may be placed in the flow delivery means to distribute the 20% ethanol solution to multiple bags, similar to the bag 15 illustrated in FIG. 2. Preferably, the manifold 40 is located downstream of the filter 20.

In a preferred embodiment of the inventive method, a 20% ethanol solution is prepared at a remote location, such as a distilled spirits plant, by mixing together in the vessel 11 one part pure ethanol and four parts pure water, preferably USP purified water, to form the 20% ethanol solution. The 20% ethanol solution is tested/assigned to verify that it has the desired specifications for bioburden and endotoxin levels. Next, 20% ethanol solution is dispensed from the vessel 11 into the transportable storage means (e.g., a bioprocess container (BPC) 15) through the tube 14 connecting the vessel 11 to the transportable storage means. The 20% ethanol solution is filtered as it passes through filter 20 located in the tube 14 connecting the vessel 11 to transportable storage means. In this embodiment of the invention, the pump 16 is used to push the 20% ethanol solution through the filter 20 and into the transportable storage means.

When the transportable storage means is filled with the 20% ethanol solution, the tubing 14 is clamped off, preferably along the third portion 14c of the tubing 14, and then cut above the clamp 30 (or, for example, detached from the outlet port 22 of the filter 20 if the third position 14c of the tubing 14 is clamped off) to transform transportable storage means into a closed system to ensure that the 20% ethanol solution contained therein remains within the desired specifications for bioburden and endotoxin levels and to free the transportable storage means for transport.

When the transportable storage means is filled with the 20% ethanol solution, the transportable storage means, if not already placed in a protective storage container 25, is placed in a protective storage container 25.

When the transportable storage means is being filled with the 20% ethanol solution, the sampling means, which preferably is provided, also is filled with the 20% ethanol solution from the vessel 11 via the tubing 14 and the tubing 24. After filling, the sampling means may be clamped off, cut from the tubing 24, and stored at the filling location, or stored and transported with the bag 15, or transported separately from the bag, as desired. The tubing 14c downstream of the tubing 24, or a portion of the tubing 24 upstream from where on the tubing 24 is clamped to clamp off the sampling means, is also clamped off prior to cutting the tubing 24 to free the sampling means, to maintain the bag 15 as a closed system. Alternatively, the sampling means may remain connected to the bag 15, via the tubing 24 and the tubing 14, and be transported with the bag 15.

After the bag 15 has been filled, clamped off, and placed within the protective storage container 25, the portion of the tubing 14 still attached to the bag 15 and any components attached thereto, such as the filter 20 and the sampling means if the tubing 14 has been clamped off above the filter 20 and the sampling means has not been clamped off and detached, are laid on top of the filled bag 15, and the lid 31 is secured onto the protective storage container 25. If the filled sampling means has already been clamped off and detached, and it is desired to store and ship it with the bag 15, the detached filled sampling means is laid on top of the filled bag 15 and lid 31 is then secured to the protective container 25.

After the lid 31 has been secured on the protective storage container 25, the protective storage container 25 with the 20% ethanol solution contained therein, is ready to be stored or shipped.

What is claimed is:

1. A method for providing 20% ethanol solutions that meet bioburden and endotoxin requirements, comprising:
   mixing in a vessel pure ethanol with USP purified water to make a 20% ethanol solution;
   testing the 20% ethanol solution for compliance with a predetermined specification for bioburden and endotoxin levels for a 20% ethanol solution;
   providing a transportable storage means;
   providing connecting means connecting the vessel to the transportable storage means, the connecting means comprising tubing;
   providing a filter means for filtering the 20% ethanol solution, said filter means being disposed in line with the connecting means and proximal to the transportable storage means;
   providing closure means for closing the connecting means to stop flow from the vessel;
   dispensing 20% ethanol solution from the vessel into the transportable storage means through the connecting means and the filter means;
   providing a container for said transportable storage means;
   placing said transportable storage means in said container; and
   transporting said container and transportable storage means containing the ethanol solution from a first location to a second location, the first location being where the ethanol solution is placed in the transportable storage means and the transportable storage means is placed into the container, and the second location being where an end user uses the ethanol solution, the second location being off-site of the first location.

2. The method of claim 1, further including
   dispensing 20% ethanol solution which is within the specification for bioburden and endotoxin levels from said transportable storage means at said second location for use in cleaning and/or storing Protein A with the 20% ethanol solution to rejuvenate the Protein A between manufacturing runs of monoclonal antibody production; and
   cleaning and/or storing Protein A with the 20% ethanol solution to rejuvenate the Protein A between manufacturing runs of monoclonal antibody production.

3. The method of claim 1, further including
providing pump means for pumping the 20% ethanol solution from the vessel into the transportable storage means, said pump means being provided upstream of the filter means; and
pumping the 20% ethanol solution using the pumping means to dispense the 20% ethanol solution from the vessel into the transportable storage means.

4. The method of claim 1, further including
providing sampling means communicating with the connecting means to receive a flow from said vessel, said sampling means being disposed downstream of said filter means and upstream of said transportable storage means, and sealing means to seal the sampling means from said connecting means.

5. The method of claim 1, further including
providing manifold means disposed downstream of said filter means for distributing flow to a plurality of transportable storage means, and
dispensing 20% ethanol solution from the vessel into the plurality of transportable storage means.

6. The method of claim 1,
wherein the filter means, a portion of connecting means, and the transportable storage means are detachable from the vessel.

7. The method of claim 1,
wherein the filter means and a portion of the connecting means are detachable from the transportable storage means.

8. The method of claim 4, wherein the sampling means is detachable from the connecting means.

9. The method of claim 1, wherein the transportable storage means is placed in the container prior to dispensing the 20% ethanol solution into the transportable storage means.

10. The method of claim 1, wherein the transportable storage means is placed in the container after dispensing the 20% ethanol solution into the transportable storage means.

11. The method of claim 1, wherein the container comprises a drum.

12. A method for providing 20% ethanol solutions that meet bioburden and endotoxin requirements, comprising:
mixing in a vessel pure ethanol with USP purified water to make a 20% ethanol solution;
testing the 20% ethanol solution for compliance with a predetermined specification for bioburden and endotoxin levels for a 20% ethanol solution;
providing a transportable storage means;
providing connecting means connecting the vessel to the transportable storage means, the connecting means comprising tubing;
providing a filter means for filtering the 20% ethanol solution, said filter means being disposed in line with the connecting means and proximal to the transportable storage means;
providing sampling means communicating with the connecting means to receive a flow from said vessel, said sampling means being disposed downstream of said filter means and upstream of said transportable storage means, and sealing means to seal the sampling means from said connecting means;
providing closure means for closing the connecting means to stop the further flow from the vessel;
providing pump means for pumping the 20% ethanol solution from the vessel into the transportable storage means and the sampling means, said pump means being provided upstream of the filter means;
pumping the 20% ethanol solution using the pumping means to dispense the 20% ethanol solution from the vessel into the transportable storage means and sampling means through the connecting means and the filter means;
providing a container for said transportable storage means;
placing said transportable storage means in said container; and
transporting said container and transportable storage means containing the ethanol solution from a first location to a second location, the first location being where the ethanol solution is placed in the transportable storage means and the transportable storage means is placed into the container, and the second location being where an end user uses the ethanol solution, the second location being off-site of the first location;
wherein the filter means, a portion of connecting means, and the transportable storage means are detachable from the vessel; and
wherein the sampling means is detachable from the connecting means.

13. The method of claim 12, further including:
providing manifold means disposed downstream of said filter means for distributing flow to a plurality of transportable storage means; and
dispensing 20% ethanol solution from the vessel into the plurality of transportable storage means.

14. The method of claim 12, wherein the transportable storage means is placed in the container prior to dispensing the 20% ethanol solution into the transportable storage means.

15. The method of claim 12, wherein the transportable storage means is placed in the container after dispensing the 20% ethanol solution into the transportable storage means.

16. The method of claim 14, further including
dispensing 20% ethanol solution which is within the specification for bioburden and endotoxin levels from said transportable storage means at said second location for use in cleaning and/or storing Protein A with the 20% ethanol solution to rejuvenate the Protein A between manufacturing runs of monoclonal antibody production; and
cleaning and/or storing Protein A with the 20% ethanol solution to rejuvenate the Protein A between manufacturing runs of monoclonal antibody production.

17. The method of claim 15, further including
dispensing 20% ethanol solution which is within the specification for bioburden and endotoxin levels from said transportable storage means at said second location for use in cleaning and/or storing Protein A with the 20% ethanol solution to rejuvenate the Protein A between manufacturing runs of monoclonal antibody production; and
cleaning and/or storing Protein A with the 20% ethanol solution to rejuvenate the Protein A between manufacturing runs of monoclonal antibody production.

18. The method of claim 12, wherein the container comprises a drum.

* * * * *